US006245553B1

(12) United States Patent
Keyser

(10) Patent No.: US 6,245,553 B1
(45) Date of Patent: Jun. 12, 2001

(54) METHOD AND APPARATUS FOR LIMITING EMISSIONS FROM A CONTAINED VESSEL

(76) Inventor: Gene E. Keyser, 3311 Scrub Oak La., Jacksonville, FL (US) 32223

(*) Notice: Subject to any disclaimer, the term of this patent is extended or adjusted under 35 U.S.C. 154(b) by 0 days.

(21) Appl. No.: 09/369,209

(22) Filed: Aug. 5, 1999

(51) Int. Cl.[7] .............................. C12M 1/21

(52) U.S. Cl. .............. 435/266; 435/300.1; 435/301.1; 422/4; 55/385.4; 96/218; 95/161; 95/174; 95/266

(58) Field of Search .............................. 435/266, 283.1, 435/289.1, 262, 300.1, 262.5, 301.1; 95/258, 160, 266, 204, 161, 176, 158, 174, 201, 173; 96/218; 55/385.4; 422/4

(56) References Cited

U.S. PATENT DOCUMENTS

| | | | | |
|---|---|---|---|---|
| 3,038,285 | * | 6/1962 | Mavrovic . | |
| 3,739,551 | | 6/1973 | Eckert | 55/90 |
| 3,778,969 | * | 12/1973 | Sudduth | 55/55 |
| 3,828,525 | | 8/1974 | Copa et al. | 55/68 |
| 3,920,794 | * | 11/1975 | La Mantia et al. | 423/242 |
| 3,969,479 | | 7/1976 | Lonnes et al. | 423/210 |
| 4,125,589 | | 11/1978 | Devries | 423/245 |
| 4,141,702 | | 2/1979 | Devries | 55/94 |
| 4,307,067 | | 12/1981 | Tagawa et al. | 423/224 |
| 4,391,704 | | 7/1983 | Anderson | 210/188 |
| 4,550,010 | | 10/1985 | Chelu | 422/4 |
| 5,077,208 | | 12/1991 | Sublette | 435/168 |
| 5,279,963 | | 1/1994 | Hobby | 435/266 |
| 5,354,545 | | 10/1994 | Buisman | 423/242.1 |
| 5,431,808 | | 7/1995 | Zumbragel | 210/188 |
| 5,634,962 | * | 6/1997 | Trahan et al. | 95/158 |
| 5,635,394 | | 6/1997 | Horn | 435/266 |
| 5,681,470 | * | 10/1997 | Safi | 210/603 |
| 5,846,274 | | 12/1998 | Smelser | 55/381 |
| 5,869,323 | | 2/1999 | Horn | 435/266 |
| 5,876,662 | | 3/1999 | Jain | 422/12 |
| 5,897,690 | * | 4/1999 | McGrew | 95/188 |
| 5,958,238 | | 9/1999 | Langerwerf | 210/603 |

* cited by examiner

*Primary Examiner*—William H. Beisner
(74) *Attorney, Agent, or Firm*—Testa, Hurwitz & Thibeault, LLP

(57) ABSTRACT

The need to filter gas emanating from a containment vessel is reduced or eliminated by maintaining, within the vessel, a gradient that concentrates most of the gaseous contaminants away from the vessel exits. This is achieved by reducing the density of gas drawn from the region near its source and discharging the reduced-density gas to another region of the vessel. Owing to its reduced density, the discharged gas already has a lower contaminant concentration than the source gas. The concentration decreases further as convection draws the discharged gas back to its source. So long as the gas flows within the containment vessel are non-turbulent, the concentration gradient remains substantially static, and the vents remain exposed only to low concentrations of contaminants. The gas density may be reduced by heating and humidification, catalytic reaction, or reaction among constituents of the gas.

30 Claims, 1 Drawing Sheet

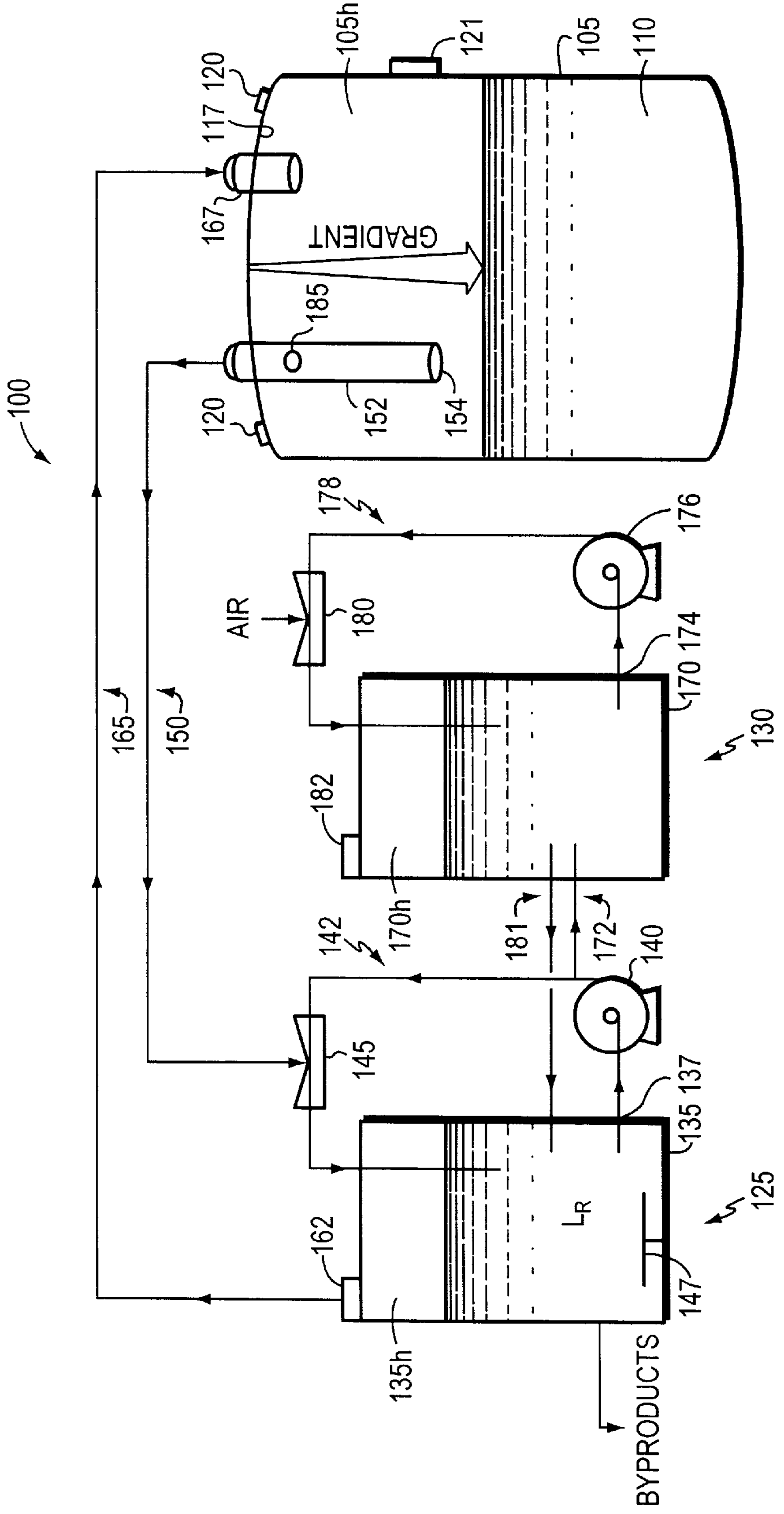
100
105h
121
105
110
120
117
167
GRADIENT
185
152
154
178
176
AIR
180
170
174
165
150
130
182
170h
181
172
142
140
145
135
137
$L_R$
125
162
147
135h
BYPRODUCTS

METHOD AND APPARATUS FOR LIMITING EMISSIONS FROM A CONTAINED VESSEL

FIELD OF THE INVENTION

The present invention relates to treatment of liquids and gases, and in particular to control of odor and emissions in a contained system.

BACKGROUND OF THE INVENTION

Waste-treatment systems may operate over a wide area, drawing sewage from numerous collection points to one or more central facilities for treatment. Offensive and even toxic gaseous emissions may be generated throughout the system wherever complete containment is impossible. For example, typical municipal waste-treatment systems utilize gravity flow to transport sewage to the central facility. In systems that serve even moderately sized areas, it is impractical to conduct waste along a single stretch of conduit from the most remote collection point to the treatment center; the declivity between end points of the conduit that would be necessary to maintain adequate flow would be too great (requiring, for example, locating the discharge point at the treatment center many feet underground). Instead, the sewage path is divided into segments short enough to require only a few feet of incline. Between segments, "lift stations" increase the height of the flowing material so that the declivity between stations can be roughly the same.

A lift station may be visualized as a large containment vessel within which the volume of liquid is periodically changed. Gas dissolved or generated in the liquid as well as vapor from the liquid rise from its surface within the vessel, and as the liquid level rises, the effect is like that of a piston: the gas is compressed and vessel pressure increases. To avoid damage to such vessels, which ordinarily cannot tolerate large pressures, some of the gas must be discharged. Odor control is therefore important. Typical systems employ filters, scrubbers, oxidation systems, and/or biosystems that reduce the concentration of offensive or environmentally deleterious material in the gas. See, e.g., U.S. Pat. No. 5,354,545. Such systems may be complex and require high throughput capacity to efficiently process large volumes of gas discharged as the liquid level rises in the vessel.

The problem of odor containment is not restricted to systems in which liquid levels vary. In waste-digestion systems, for example, internal pressure may increase as a result of the biological processes utilized to treat the waste, which create gaseous byproducts. The volumes of gas generated may vary substantially over the treatment cycle, necessitating frequent venting and, as a result, the use of filtration systems capable of processing the peak levels in order to maintain constant internal pressure.

DESCRIPTION OF THE INVENTION

Brief Summary of The Invention

In accordance with the present invention, the need for gas filtration is reduced or eliminated by maintaining, within a containment vessel, conditions that concentrate most of the gaseous contaminants away from the vessel exits. In one embodiment, this is achieved by continuously heating and humidifying gas drawn from the region near its source (typically the surface of the liquid in the vessel) and discharging the hot, moist gas to another region of the vessel—usually nearer the vents. The discharged gas already has a reduced density and therefore a lower contaminant concentration relative to the source gas. In the general area of the discharge, the concentration decreases further as convection draws the discharged gas back to its source. So long as the gas flows within the containment vessel are non-turbulent, this concentration gradient remains substantially static, and the vents remain exposed only to low concentrations of contaminants.

In a second embodiment, the amount of gas in the containment vessel is reduced in molar amount prior to being re-introduced. This may be accomplished by reacting the gas with a catalyst or otherwise causing constituents thereof to assume solid or liquid form, or by causing gaseous constituents to react with one another so as to reduce the molar amount of gas, or by a combination of these techniques. Once again, a concentration gradient is established between the regions of gas withdrawal and re-introduction, and non-turbulent gas flows ensure that this concentration gradient remains substantially static.

In accordance with either embodiment, the amount of gas that must be actively withdrawn from the system is limited. Even in a variable-volume system, such as a lift station, it is generally unnecessary to process gaseous volumes equivalent to all of the discharged gas. Instead, moderate increases in liquid levels that do not create gas turbulence will not substantially degrade the quality of the air at the vents, since the additional discharged air still arrives from the low-concentration side of the gradient. Continuous, low-volume processing in effect creates a largely static internal environment that obviates or at least reduces the need for outflow processing.

Accordingly, in a first aspect, the invention comprises a method of limiting gaseous emissions from a containment vessel. Gas is withdrawn from a first location within the containment vessel, and the withdrawn gas is heated and moistened, caused to react so as to decrease in molar volume, or both. At least a fraction of the treated gas is returned into the containment vessel at a second location therein. The withdrawal and return of gas are preferably conducted so as to create a substantially unchanging gas-concentration gradient between the first and second locations. In some embodiments, an external arrangement recirculates heated liquid past a gas venturi which is fluidly coupled to the containment vessel and provides the suction to withdraw gas therefrom. The gas enters the recirculating liquid stream and is returned with vapor derived from the stream. Alternatively, the gas may be heated and moistened by a humidifier arrangement contained entirely within the vessel.

In accordance with the second embodiment, the withdrawn gas may be treated to deplete, reduce, or chemically modify constituents thereof. For example, the recirculating liquid in the just-described venturi arrangement may be charged with digestive microorganisms or an abiotic catalyst, so that the vapor derived from the liquid has a reduced concentration of undesirable constituents. It should be noted that the catalyzed reaction need not be limited to the undesirable gaseous components. If any of the components of the withdrawn gas are reduced in molar amount (e.g., sequestered from gas phase entirely by conversion to liquids and/or solids) or reactively combined such that the molar volume of returned gas is less than that withdrawn, a concentration gradient will result; the site of gas re-introduction is chosen such that this gradient places cleaner air near points of possible emission from the vessel. Moreover, if the level of the liquid in the vessel is not rising, the gradient will cause clean air to be drawn into the containment vessel from the external environment, precluding emissions from the vessel. As with the first embodiment, gas processing can take place externally or within the vessel.

In a second aspect, the invention comprises hardware arrangements for accomplishing the foregoing methods.

BRIEF DESCRIPTION OF THE DRAWINGS

The foregoing discussion will be understood more readily from the following detailed description of the invention, when taken in conjunction with the single FIGURE of the drawing, which schematically illustrates a system in accordance with the invention.

DETAILED DESCRIPTION OF THE PREFERRED EMBODIMENTS

With reference to the FIGURE, a system 100 is adapted for use with a containment vessel 105, which contains a quantity of a liquid 110. Gaseous components originating with liquid 110 reside in the headspace 105*h* between the surface of liquid 110 and the ceiling 117 of vessel 105. As the height of liquid 110 rises, or with increased chemical activity therein, the amount of gas in headspace 105*h* increases. In order to avoid damage to vessel 105, excess gas is vented through a series of ceiling and/or side vents representatively shown at 120, 121.

The illustrated hardware arrangement comprises a gas withdrawal and return subsystem 125 and an optional catalyst-recovery subsystem 130. Subsystem 125 comprises a vessel 135 for containing a recirculation liquid $L_R$. Vessel 135 includes liquid outlet 137 leading to a recirculation pump 140. Pump 140 displaces the liquid $L_R$ along a flow path 142, which leads back to vessel 135 through a gas venturi 145. The speed of pump 140 depends on the volume of vessel 105 and the requirements of venturi 145. Because it is typically necessary to withdraw only moderate volumes of gas from headspace 105*h*, substantial operating speeds are not ordinarily necessary. For example, using a 3-in conduit along recirculation path 142, a flow rate ranging from 35–90 gal/min is generally adequate for headspace cross-sectional areas ranging from 150–300 $ft^2$ while moving 25–75 scfm of gas. In accordance with the first embodiment of the invention, which relies on heating and humidification of gas influent, energy from the hydraulic inefficiency of pump 140 (and the heat given off by its motor when a submersible pump is used), as well as any heat of reaction of constituents of the withdrawn gas, are generally enough to raise the temperature of liquid $L_R$ so as to adequately heat the withdrawn gas; in general, an operating temperature 10–70° F. higher than that of the gaseous influent is desirable. If the heat generated in this fashion is insufficient, a heating fixture 147 may be employed.

Gas from headspace 105*h* is drawn into venturi 145 along a flow path 150. Preferably, the terminus of flow path 150 at vessel 105 comprises a vertical conduit that descends into the interior of vessel 105 so that its open port 154 draws gas from near the surface of liquid 110. As withdrawn gas enters venturi 145, it mixes with and becomes entrained within the heated recirculation liquid $L_R$. At least a portion of the gas comes out of solution and is released, along with the vapor of liquid $L_R$, into the headspace 135*h* of vessel 135. The relative amounts of withdrawn gas and evaporated liquid $L_R$ in headspace 135*h* depend on the solubility of the gas within liquid $L_R$, the vapor pressure of liquid $L_R$, and the temperature at which the liquid is maintained by heating fixture 147. As described below, the fraction of withdrawn gas within the vapor can be reduced further by including reactive and/or catalytic components within liquid $L_R$. Typically, liquid $L_R$ is water or an aqueous solution (or suspension), and headspace 135*h* contains both water vapor and residual components from the withdrawn gas.

Vapor from headspace 135*h* is allowed to return to vessel 105 through a gas outlet 162, which leads to a flow path 165. Selection of the size of flow path 165 will determine any restrictions placed on the gas return flow and may desirably increase the pressure (relative to atmospheric) within headspace 135*h*. The terminus of flow path 165 at vessel 105 may be an inlet 167 located near ceiling 117, so that gas re-enters vessel 105 in the general vicinity (i.e., at a similar height) of vents 120, 121. In operation, gas withdrawn through conduit 152 is rich in gaseous effluent due to proximity to the gas source, i.e., liquid 110. Vapor returned through inlet 167 has a lower density due to its elevated temperature and, as a result, contains a lower concentration of the original gaseous constituents than gas withdrawn through port 154. This is so even if none of the withdrawn gas has dissolved or reacted in liquid $L_R$. The concentration of objectionable gaseous constituents, then, is necessarily lower in the vicinity of inlet 167 than in the vicinity of port 154.

The elevated temperature of returning vapor relative to liquid 110 causes the incoming vapor to flow toward the surface of liquid 110, where it condenses. This convective flow, if undisturbed by turbulent withdrawal or return of gas, causes a concentration gradient to form between inlet 167 and the surface of liquid 110. It is found, surprisingly, that the concentration at vents 120 of gaseous constituents from liquid 110 is even smaller than the concentration in vapor returned through inlet 167. Of course, that concentration can be made smaller still by causing withdrawn gas to be retained or reacted within liquid $L_R$.

In accordance with the second embodiment of the invention, the total molar amount of gas is reduced before its re-introduction into vessel 105; this may or may not be accompanied by heating and humidification as described above. For example, if the primary offensive constituent of the gaseous effluent is hydrogen sulfide ($H_2S$), then iron or iron compounds, which act catalytically, may be dissolved or suspended liquid $L_R$. In particular, ferrous ($Fe^{2+}$) compounds react with $H_2S$ to form FeS, which, in the presence of oxygen, itself reacts to form $Fe_2S_3$. That compound, in turn, decomposes into ferrous ion and elemental sulfur. Similar action may be obtained through use of copper, cobalt, and their compounds. Alternatively, conventional biological solids (e.g., Beggiatoa and/or Thiobacillus and/or Thiothryx) that oxidize $H_2S$ into elemental sulfur in the presence of oxygen may instead be dispersed in liquid $L_R$. Both of these processes reduce the total amount of gas being returned to vessel 105, as well as the offensive component therein.

In either case, it is generally necessary to continuously replenish oxygen in liquid $L_R$ to avoid overwhelming the catalyst or bacteria (thereby reducing both the efficiency of the process and the uptake of $H_2S$ by the liquid) and to ensure complete reaction therewith. In a simple implementation, subsystem 130 is omitted, and oxygen is replenished to the system by entry through vents 120, 121. Alternatively, as shown in the FIGURE, a small sidestream of the recirculating liquid can be diverted to recovery subsystem 130, which introduces air, oxygen, or another oxidant therein. In a representative implementation, a valve or Y-connector along flow path 142 directs a portion of the flow to a recirculation vessel 170 by means of a first auxiliary flow path 172. Vessel 170 may contain a volume of water or other aqueous mixture. A liquid outlet 174 leads to a recirculation pump 176, which displaces the liquid from vessel 170 along a flow path 178, which leads back to the vessel through a gas venturi 180. The flow rate through path 178 and the characteristics of venturi 180 are chosen so as to cause continuous introduction of an optimal amount of air into the recirculating liquid. Liquid is returned to vessel 135 through a second auxiliary flow path 181 at a rate corresponding to the withdrawal rate through first auxiliary flow path 172. Accumulated elemental sulfur is periodically collected from vessel 135. Added ro excess gases introduced through venturi 180 may be released separately from the headspace 170*h* of vessel 170 through a vent 182 so as to ensure that more gas is withdrawn than is returned. The subsystem 130 is particularly useful when gases treated in subsystem 125 are sensitive to the presence of excess oxygen or other component of gases introduced through venturi 180.

Indeed, such sensitivity can be exploited to cause reaction among constituents of the gas, thereby reducing its molar volume without the need to actually withdraw constituents from the mixture. For example, ammonia in the gas mixture reacts with oxygen according to the formula $$4NH_3+5O_2\rightarrow 4NO+6H_2O$$

At fully saturated ambient humidity levels, the water vapor leaves the gas phase, thereby reducing the molar amount of gas re-introduced into vessel 105.

When used in conjunction with a vessel in which the volume (and therefore the height) of liquid varies, the length of conduit 152 may be chosen such that port 154 lies just above a maximum expected or maximum average liquid level. In such an implementation, it is preferred to include a vacuum relief or safety inlet 185 leading directly into flow path 150. Safety inlet 185 is located a sufficient distance above liquid 110 to preclude the possibility of being reached by the liquid, and may be no more than an aperture through conduit 152. If the level of liquid 110 rises above port 154, the fluid path through inlet 185 will prevent liquid from being drawn into flow path 150. Inlet 185 has a diameter substantially smaller than that of conduit 152, since during normal operation it competes with port 154 for withdrawal of gas. Preferably, the diameter of conduit 152 is at least four times that of inlet 185 (as determined by the relative heights of venturi 145, port 154, and inlet 185). Only if venturi 145 is located more than 33.9 ft (corresponding to atmospheric pressure) above the absolute maximum liquid level is inlet 185 not required.

It should be emphasized that the illustrated subsystem 125 represents a preferred approach; mechanical or other suitable vacuum systems not utilizing a venturi arrangement can instead be used. The objectives of gas heating and humidification, followed by release into a vessel region remote from the gas source, do not require an external system. A gas suction, humidifier, and discharge arrangement can instead be located within vessel 105, withdrawing gas and discharging vapor at locations corresponding to those shown in the FIGURE. Similar reasoning applies to catalyzed or other reactions involving constituents of the gas in headspace 105*h*. For example, the gas may be passed through an internal or external biofilter and returned as described above.

In a representative implementation, a containment vessel used as a lift station had a diameter of 20 ft and a depth of 45 ft, and was characterized by highly offensive and sometimes hazardous levels of $H_2S$ emissions. The structure was charged by liquid from a gravity sewer main entering the containment through a 4-ft diameter portal located about 15 ft from the containment bottom, with approximately ¼–½ of the opening normally open to the atmosphere. The entering liquid fell approximately 4–5 ft into the liquid level maintained in the containment, the level varying with both the influent flows and discharge flows as normally observed in these structures. Furthermore, while covers for the access doors were kept in place, two 6-in ventilation ports were attached through the ceiling of the containment.

The typical flow entering the lift station ranged from 5–15 million gallons per day (mgd), being discharged by pumps internal to the containment via piping to the treatment facility several miles distant. Typical $H_2S$ levels throughout the interior of the containment were in excess of 200 ppm (volume/volume) and routinely exceeded 1000 ppm. Measured at the side entrance portal, $H_2S$ escaping from the containment typically was in the range of 15–25 ppm with numerous excursions in excess of 50 ppm. The exit gas variations exhibited diurnal variance, as well as daily and weekly variance, in addition to those caused by the piston effect of changing liquid levels. An arrangement as shown in the FIGURE was assembled at the structure with a 4-in pipe serving as conduit 152 placed below the midline of the side portal; the opening at the end of this conduit was disposed about 4 ft above the surface of the liquid. Gas was returned from subsystem 125 through 4-in and then 3-in conduits, entering the containment structure through the ceiling. The 6-in ceiling vents to the structure were closed but the penetrations of the suction and return conduits were not gas-tight connections. Operating the system with water only and without catalysts or treatment processes therein, the gases entering conduit 152 were reduced in $H_2S$ concentration to 15–25 ppm and thereafter to a steady-state level of 3 ppm, although sampling the gas immediately above the liquid level revealed the same values (200–1000 ppm) as previously observed throughout the structure. The gases re-entering the containment vessel from subsystem 125 also had a $H_2S$ concentration of 3 ppm (confirming the absence of catalytic removal in subsystem 125), while gas exiting the containment vessel through the portal (as a result of changes in liquid level within the structure and diurnal variances) were reduced to 1–3 ppm.

Gas was removed from the containment vessel at a rate of 50 scfm at a temperature of 65–80° F. and a relative humidity of 100%; the returned gas had a temperature of 110–115° F. (representing the operating temperature of subsystem 125) and a relative humidity of 100%. By establishing a laminar flow regime directing and confining the offensive $H_2S$ to its original source, the emissions from the structure were reduced. The 50 scfm of gas circulated from top to bottom by virtue of its lower density in the return flow and its low cross-sectional velocity ($<0.003$ ft/sec). The temperature gradient further enhanced the suppression of odorous emissions from the source as the warm humid air was drawn by condensation to the cooler contained liquid, thus creating convective flow in the direction of the original source of the $H_2S$. When the ceiling vents of the structure were opened, the density and condensation gradient were superseded by the ventilation airflow; while ambient air ($<0.0001$ ppm $H_2S$) entered the portal on the side of the structure, a sustained flow of $>50$ ppm $H_2S$ was emitted from the ceiling vents.

The effect of gas sequestration was tested by adding iron oxide to the recirculating water $L_R$ (ca. 1 mg/liter as both suspended solids and dissolved solids), whereupon generation of elemental sulfur as a colloidal solid in suspension was observed with a concurrent oxygen demand such that the $H_2S$ conducted to the device averaged nominally 3 ppm and the returning gas averaged $<0.1$ ppm. The catalytic nature of iron (and numerous other metals) to enhance the oxidation of $H_2S$ to elemental sulfur and to a lesser extent to sulfuric acid is well known. There was observed a net inflow of ambient air into the structure through the portals, albeit at velocities of 0.1–1 ft/sec, and no gas exited from the device, resulting in no detectable discharge of offensive matter ($H_2S$ and other odoriferous material) from the structure. A portion of the concentrated suspension of sulfur was periodically (weekly) discharged from vessel 135 to the liquid sewage in the structure and replaced by fresh water, and the subsystem 125 was continuously maintained to its full capacity by make-up water to replace those amounts lost to evaporation.

In another experiment, the water in subsystem 125 was replaced with a suspension of activated sludge originally having a suspended solids concentration of 550 mg/liter. Results similar to that observed with the addition of iron were obtained.

In a third experiment, the water in subsystem 125 contained both a suspension of activated sludge originally having a suspended solids concentration of 50 mg/liter and approximately 1 mg/liter of iron oxide. The observed return and concentration of $H_2S$ was substantially less than 0.01 ppm and $H_2S$ was not detectable (<0.0001 ppm) at any time in the immediate vicinity of the openings into the structure.

The addition of a catalyst-recovery subsystem 130 allows air to be introduced in limited amounts to oxidize the ferrous sulfide (resulting from reaction with $H_2S$) to ferric sulfide with concomitant decomposition to elemental sulfur and ferrous hydroxide. If the withdrawn gas also contains nitrogen and carbon dioxide, these are largely dissolved as the gas enters subsystem 125. By introducing air through venturi 180 and venting vessel 170 separately through vent 182, a large portion of these gases is prevented from returning to the containment vesse—thereby further reducing emissions therefrom—and may be disposed of in a conventional fashion. This is particularly the case when headspace 135*h* is maintained at an elevated temperature relative to headspace 170*h*, and when limited amounts of air are used with amounts of oxygen sufficient only to oxidize the influent $H_2S$ via the metal and/or biological catalyst.

It will therefore be seen that the foregoing approach to containment of gaseous effluent is conveniently practiced and readily applied to a variety of different environments. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of limiting gaseous emissions from a containment vessel, the method comprising the steps of:

a. withdrawing gas from a first location at a first height within the containment vessel;

b. processing the withdrawn gas to reduce its density; and c. returning at least a fraction of reduced-density gas into the containment vessel at a second location at a second height therein, the first height being lower than the second height, the withdrawal and return of gas cooperating so as to restrict the gas concentration at the second location and to create a substantially unchanging gas-concentration gradient decreasing from the first location to the second location, the gradient being maintained through non-turbulent withdrawal and return of gas.

2. The method of claim 1 wherein the withdrawn gas has a molar volume, the density being reduced by reducing the molar volume of the withdrawn gas.

3. The method of claim 2 wherein the molar volume is reduced by catalytically reacting the gas to produce at least one reaction product sequestered from the gas phase.

4. The method of claim 2 wherein the molar volume is reduced by causing constituents of the gas to react with each other.

5. A method of limiting gaseous emissions from a containment vessel, the method comprising the steps of:

a. withdrawing gas from a first location within the containment vessel;

b. heating and moistening the withdrawn gas to reduce its density; and c. returning at least a fraction of reduced-density gas into the containment vessel at a second location therein, the withdrawal and return of gas cooperating so as to restrict the gas concentration at the second location, by heating and moistening the withdrawn gas.

6. A method of limiting gaseous emissions from a containment vessel, the method comprising the steps of:

a. withdrawing gas from a first location within the containment vessel by means of a suction created by recirculating liquid through a venturi, the venturi being fluidly coupled to the first location, the recirculating liquid comprising for material for reacting with gas drawn from the solution;

b. processing the withdrawn gas to reduce its density through reaction with the material in the recirculating liquid; and c. returning at least a fraction of reduced-density gas into the containment vessel at a second location therein, the returned vapor containing a lesser amount of gas than that withdrawn from the vessel, the withdrawal and return of gas cooperating so as to restrict the gas concentration at the second location.

7. The method of claim 6 wherein the material comprises a catalyst.

8. The method of claim 7 wherein the material comprises microorganisms.

9. The method of claim 7 wherein the catalyst is suspended or dissolved.

10. The method of claim 7 further comprising the step of diverting a portion of the recirculating liquid through a catalyst-recovery system.

11. A method of limiting gaseous emissions from a containment vessel, the method comprising the steps of:

a. withdrawing gas from a first location within the containment vessel by means of a suction created by recirculating liquid through a venturi, the venturi being fluidly coupled to the first location;

b. heating the recirculating liquid to reduce the density of the withdrawn gas; and c. re-introducing into the vessel vapor from the liquid at the second location, at least some of the withdrawn gas being entrained therein.

12. A method of limiting gaseous emissions from a containment vessel, the method comprising the steps of:

a. withdrawing gas from a first location within the containment vessel, the first location being situated at a first height;

b. processing the withdrawn gas to reduce its density; and c. returning at least a fraction of reduced-density gas into the containment vessel at a second location therein, the second location being situated at a second height within the vessel, the first height being lower than the second location, the withdrawal and return of gas cooperating so as to restrict the gas concentration at the second location.

13. The method of claim 12 wherein the vessel comprises a variable volume of liquid beneath a headspace containing the gas, convection drawing the returned gas to the liquid surface.

14. The method of claim 13 wherein the first location is at least as high as an average level of the liquid in the vessel, and further comprising the steps of:

a. withdrawing the gas by means of a suction created by recirculating heated liquid through a venturi, the venturi being fluidly coupled to the first location by means of a withdrawal conduit having a diameter;

b. providing a safety opening at a height above the first location and at least as high as a maximum allowable liquid level within the vessel, the safety opening having a diameter smaller than the diameter of the withdrawal conduit and being fluidly coupled to the venturi, thereby preventing introduction of vessel liquid into the venturi when the vessel liquid rises above the first location; and c. re-introducing into the vessel vapor from the heated liquid at the second location, the returned, gas being entrained therein.

15. The method of claim 14 wherein the diameter of the withdrawal conduit is at least four times the diameter of the safety opening.

16. Apparatus for limiting gaseous emissions from a containment vessel, the apparatus comprising:

a. means for withdrawing gas from a first location at a first height within the containment vessel;

b. means for processing the withdrawn gas to reduce its density; and c. means for returning at least a fraction of the reduced-density gas into the containment vessel at a second location at a second height therein, the first height being lower than the second height, the withdrawal and return of gas cooperating so as to restrict the gas concentration at the second location and to create a substantially unchanging gas-concentration gradient decreasing from the first location to the second location, the gradient being maintained by non-turbulent gas flow.

17. The apparatus of claim 16 wherein the withdrawn gas has a molar volume and further comprising means for reducing the density by reducing the molar volume of the withdrawn gas.

18. The apparatus of claim 17 wherein the means for reducing density comprises means for catalytically reacting the gas to produce at least one reaction product sequestered from the gas phase.

19. The apparatus of claim 17 wherein the means for reducing density comprises means for causing constituents of the gas to react with each other.

20. Apparatus for limiting gaseous emissions from a containment vessel, the apparatus comprising:

a. means for withdrawing gas from a first location within the containment vessel;

b. means for heating and moistening the withdrawn gas to reduce its density; and c. means for returning at least a fraction of the reduced-density gas into the containment vessel at a second location therein, the withdrawal and return of gas cooperating so as to restrict the gas concentration at the second location.

21. Apparatus for limiting gaseous emissions from a containment vessel, the apparatus comprising:

a. a recirculation subsystem for withdrawing gas from a first location within the containment vessel and returning gas to a second location within the containment. vessel, the recirculation subsystem comprising (i) a venturi fluidly coupled to the first location for withdrawing gas therefrom, and (ii) means for re-introducing into the vessel at the second location vapor from the liquid, the recirculating liquid comprising a material for reacting with gas drawn from the solution so that the re-introduced vapor contains a lesser amount of gas than that withdrawn from the vessel, wherein b. the withdrawal and return of gas cooperate so as to restrict the gas concentration at the second location.

22. The apparatus of claim 21 further comprising means for heating the liquid.

23. The apparatus of claim 21 wherein the material comprises a catalyst.

24. The apparatus of claim 23 wherein the material comprises microorganisms.

25. The apparatus of claim 23 wherein the catalyst is suspended or dissolved.

26. The apparatus of claim 23 further comprising a catalyst-recovery system and means for diverting a portion of the recirculating liquid therethrough.

27. Apparatus for limiting gaseous emissions from a containment vessel, the apparatus comprising:

a. means for withdrawing gas from a first location within the containment vessel, the first location being situated at a first height;

b. means for processing the withdrawn gas to reduce its density; and c. means for returning at least a fraction of the reduced-density gas into the containment vessel at a second location therein, the second location being situated at a second height within the vessel, the first height being lower than the second height, the withdrawal and return of gas cooperating so as to restrict the gas concentration at the second location.

28. The apparatus of claim 27 wherein the vessel comprises a variable volume of liquid beneath a headspace containing the gas, convection drawing the returned gas to the liquid surface.

29. The apparatus of claim 28 wherein the first location is at least as high as an average level of the liquid in the vessel and gas is withdrawn from the vessel by means of a suction created by recirculating heated liquid through a venturi, the venturi being fluidly coupled to the first location by means of a withdrawal conduit having a diameter, and further comprising a safety opening at a height above the first location and at least as high as a maximum allowable liquid level within the vessel, the safety opening having a diameter smaller than the diameter of the withdrawal conduit and being fluidly coupled to the venturi, thereby preventing introduction of vessel liquid into the venturi when the vessel liquid rises above the first location.

30. The apparatus of claim 29 wherein the diameter of the withdrawal conduit is at least four times the diameter of the safety opening.

* * * * *